(12) United States Patent
Becker

(10) Patent No.: US 12,667,068 B2
(45) Date of Patent: Jun. 30, 2026

(54) WHEAT VARIETY B16#12-9381

(71) Applicant: Grow Pro Genetics, LLC, Hamel, IL (US)

(72) Inventor: Allen W. Becker, Hamel, IL (US)

(73) Assignee: GROW PRO GENETICS, LLC, Hamel, IL (US)

( * ) Notice: Subject to any disclaimer, the term of this patent is extended or adjusted under 35 U.S.C. 154(b) by 258 days.

(21) Appl. No.: 17/803,976

(22) Filed: Feb. 9, 2023

(65) Prior Publication Data

US 2024/0268295 A1 Aug. 15, 2024

(51) Int. Cl.
*A01H 5/10* (2018.01)
*A01H 6/46* (2018.01)

(52) U.S. Cl.
CPC ............. *A01H 6/4678* (2018.05); *A01H 5/10* (2013.01)

(58) Field of Classification Search
None
See application file for complete search history.

(56) References Cited

U.S. PATENT DOCUMENTS

| | | | |
|---|---|---|---|
| 8,809,654 B1 | 8/2014 | Lively et al. | |
| 9,282,712 B1 | 3/2016 | Marshall et al. | |
| 9,872,459 B2 | 1/2018 | Moreno-Sevilla | |
| 10,568,282 B2 | 2/2020 | Gray | |
| 11,206,785 B1 * | 12/2021 | Clarkson | A01H 5/10 |
| 2021/0059150 A1 | 3/2021 | Clarkson et al. | |
| 2025/0017162 A1 | 1/2025 | Auld et al. | |

OTHER PUBLICATIONS

Fehr et al., 1991, Principle of Cultivar Development vol. 1, Ch. 28, p. 360-366.*
U.S. Office Action mailed Jun. 16, 2025 and issued in connection with U.S. Appl. No. 17/803,977, 15 pages.
Fehr, et al. (Published: 1991, Book: Principle of Cultivar Development vol. 1, Chapter: Backcross Method, pp. 360-366). (Year: 1991).
Großkinsky et al. (2015) J. Exp. Bot. 66:5429-40.
Haun et al. (2011) Plant Physiol. 155:645-55.
Fehr (1987) ("Backcross Method" in Principles of Cultivar Development (Macmillan Pub. Co. (New York)) pp. 360-376).

* cited by examiner

*Primary Examiner* — Jason Deveau Rosen
(74) *Attorney, Agent, or Firm* — Barnes & Thornburg LLP

(57) ABSTRACT

The instant disclosure relates to the field of wheat (*Triticum aestivum* L.) breeding, specifically relating to a wheat variety designated B16#12-9381, the plants and seeds of wheat variety B16#12-9381, methods for producing a wheat plant produced by crossing the variety B16#12-9381 with another wheat plant, and hybrid wheat seeds and plants produced by crossing the variety B16#12-9381 with another wheat line or plant, and the creation of variants by backcrossing of variety B16#12-9381 are disclosed. Methods for producing other wheat varieties or breeding lines derived from wheat variety B16#12-9381 and to wheat varieties or breeding lines produced by those methods are also provided.

10 Claims, No Drawings

WHEAT VARIETY B16#12-9381

FIELD

The instant disclosure relates to the field of wheat (*Triticum aestivum* L.) breeding, specifically relating to a wheat variety designated B16#12-9381.

BACKGROUND

Wheat is one of the most widely grown food crops in the word. Cultivation adaptability and high yield make cereal grain obtained from wheat a staple food globally. There are seven species of wheat, the most widely grown (common wheat) is *Triticum aestivum*. Grain hardness generally dictates how wheat is used, with hard wheats such as hard red winter and hard red spring used in breads and crackers, and soft wheats such as soft red winter and soft white primarily used for cookies and pastries. Common wheat or "bread wheat" is most often used in bread and food products in the form of flour and is high in protein and dietary fiber. Gluten protein contributes to the unique viscoelasticity of wheat which confers its characteristic desirable dough forming properties.

Novel wheat varieties are developed with the goal of improving variety of desirable traits, including increased yield, drought and heat tolerance, pest and disease resistance, and overall improved agronomic traits. Furthermore, grain quality of wheat for four and milling and processing is also desired, such as low protein content, low water absorption, and dough spread and volume during baking.

SUMMARY

In one embodiment described herein is a plant, plant part, seed, or plant cell of wheat variety B16#12-9381, representative seed of said variety having been deposited under ATCC accession number PTA-127364. In one aspect is a wheat seed produced from (i) selfing the plant or plant part described herein or (ii) crossing of the plant or plant part described herein once with a different wheat plant or plant part. In another aspect is a wheat plant or plant part produced by growing the wheat seed as described herein. In another aspect of the wheat seed described herein, the seed is an F1 hybrid wheat seed.

In another aspect is a method of producing a progeny seed, the method comprising crossing the wheat plant described herein, to a plant of wheat variety B16#12-9381, representative seed of said variety having been deposited under ATCC accession number PTA-127364 and producing a progeny seed. In one aspect the method further comprises crossing a plant grown from the progeny seed to a plant of wheat variety of B16#12-9381 and producing a back-crossed seed. In another aspect is the backcrossed seed produced by the method described herein.

In another aspect is a method for producing a second wheat plant, the method comprising applying plant breeding techniques to the wheat plant or plant part as described herein, wherein application of said techniques results in the production of a second wheat plant. In one aspect of a method of producing a second wheat plant, the method comprising a doubling haploid seed generated from a cross of the wheat plant or plant part describe herein, with a different wheat plant.

In another aspect is a method comprising the seed as described herein. In one aspect, the seed further comprises a seed treatment on the surface of the seed.

DETAILED DESCRIPTION OF THE DISCLOSURE

The present disclosure relates to a novel wheat (*Triticum aestivum* L.) variety, designated as B16#12-9381, its seeds, plants, plant parts, and hybrids. Also provided herein are methods for producing B16#12-9381.

It is to be understood that the phraseology and terminology used herein is for the purpose of description and should not be regarded as limiting. As used herein, the terms "including," "comprising," or "having" and variations thereof herein are meant to encompass the items listed thereafter and equivalents thereof as well as additional items.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

As used herein the term "homozygous plant" as used herein is a plant with homozygous genes at 95% or more of its loci.

As used herein, the term "plant parts" includes, without limitation, plant protoplasts, plant cell tissue cultures from which wheat plants can be regenerated, plant calli, plant clumps, plant cells, embryos, pollen, ovules, pericarp, seed, flowers, florets, heads, spikes, stems, stalks, leaves, roots, root tips, anthers, and the like. When indicating that a plant is crossed or selfed this indicates that any plant part of the plant can be used. For instance the plant part does not need to be attached to the plant during the crossing or selfing, only the pollen might be used.

It also is understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

Wheat varieties should be highly homozygous and easily reproducible. Crosses between two different homozygous lines may produce uniform hybrid plants that may be heterozygous for many gene loci, while crosses between heterozygous plants may result in genetically diverse plants that are not uniform. However, plants that are self-pollinated and selected over many generations may become homozygous at almost all genetic loci and thus produce uniform populations of true breeding progeny. The term "homozygous plant" as used herein is a plant with homozygous genes at 95% or more of its loci.

The type of breeding or selection methods depends on the mode of plant reproduction, the trait(s) being improved, and the type of variety used commercially (e.g., F1 hybrid variety, pureline variety, etc.). For highly heritable traits, a choice of superior individual plants evaluated at a single location will be effective, whereas for traits with low heritability, selection may be based on mean values obtained from replicated evaluations of families of related plants. Popular selection methods which may be used for the wheat variety described herein include pedigree selection, modified pedigree selection, mass selection, and recurrent selection.

Inheritance patterns may also impact the choice of the breeding methodology. For example, pedigree breeding, backcross breeding, single seed descent, and bulk breeding, which of which are each described in U.S. Pat. No. 8,809,654 (incorporated herein by reference with regard to such background teaching), may be used. Each wheat breeding program may include a periodic, objective evaluation of the efficiency of the breeding procedure. Evaluation criteria vary depending on the goal and objectives, but may include gain from selection per year based on comparisons to an appropriate standard, overall value of the advanced breeding lines, and number of successful varieties produced per unit of input (e.g., per year, per dollar expended, etc.).

Various recurrent selection techniques may be used to improve quantitatively inherited traits controlled by numerous genes. The use of recurrent selection in self-pollinating crops may depend on the ease of pollination and the number of hybrid offspring from each successful cross. Recurrent selection may be used to improve populations of either self- or cross-pollinated crops. A genetically variable population of heterozygous individuals may either be identified or created by intercrossing several different parents. The best plants may be selected based on individual superiority, outstanding progeny, or excellent combining ability. The selected plants may be intercrossed to produce a new population in which further cycles of selection are continued. Plants from the populations may be selected and selfed to create new varieties.

Wheat variety B16#12-9381 may be used as either the female or male parent in bi-parental crosses in order to develop new and valuable wheat varieties or hybrids. Wheat normally self-pollinates in nature. Cross pollination of one wheat plant with another to produce progeny with a new combination of genetic traits, may be carried out according to methods known to those skilled in the art. Wheat cross-pollination may be achieved by emasculating flowers of a designated female plant and pollinating the female parent with pollen from the designated male parent. Methods of cross-pollinating wheat plants for use in selection and advancement are described, for example in U.S. Pat. No. 9,282,712, the disclosure of which is incorporated herein by reference with regard to such background teaching.

Plant breeding methods may also include analysis and characterization of plant genome using well known lab techniques, including, but not limited to, Starch Gel Electrophoresis, Isozyme Electrophoresis, Restriction Fragment Length Polymorphism (RFLPs), Randomly Amplified Polymorphic DNAs (RAPDs), DNA Amplification Fingerprinting (DAF), Simple Sequence Repeats (SSRs) and Single Nucleotide Polymorphisms (SNPs). Molecular markers associated with alleles of interest may also be used to select for plants that contain those alleles during crossing or breeding programs.

Molecular markers may be used during the breeding process for the selection of qualitative traits. For example, markers closely linked to alleles or markers containing sequences within the actual alleles of interest can be used to select plants that contain the alleles of interest during a crossing or backcrossing breeding program. The markers may also be used to select for the genome of the recurrent parent and against the markers of the donor parent. Using this procedure can minimize the amount of genome from the donor parent that remains in the selected plants. It can also be used to reduce the number of crosses back to the recurrent parent needed in a backcrossing program.

Genetic markers have been used for a decade or more in helping to select superior lines based on genotype. Markers for genes that may be utilized to identify specific traits include, but are not limited to: stripe (yellow) rust resistance, leaf rust resistance, barley yellow dwarf resistance, powdery mildew resistance, soil borne mosaic virus resistance, fusarium head blight resistance, stem rust resistance, photoperiod sensitivity, plant height/dwarfing, vernalization, grain color, and high kernel weight.

Double haploid breeding systems may be used for the development of homozygous lines in breeding programs and are produced by the doubling of a set of chromosomes from a heterozygous plant to produce completely homozygous progeny. Doubled haploidization is a well-known and published process used to create pure lines from segregating populations (Wong et al., 2017; Inagaki, M. N, 2003, incorporated by reference with regard to such background teaching). Thus, double haploid breeding offers the advantage of foregoing generations of selfing required to obtain a homozygous plant from a heterozygous source.

Wheat variety B16#12-9381 may be crossed with one or more parental lines, followed by repeated selfing and Selection, producing many new genetic combinations. Wheat variety B16#12-9381 may also be created using a doubled haploid breeding system. Selected germplasm may then be grown under unique and different geographical, climatic and soil conditions with further selections being made during and at the end of the growing season.

Wheat varieties that are highly homogeneous, homozygous and reproducible are useful as commercial varieties. There are many analytical methods, such as those described herein, which may be used to determine the homozygotic stability, phenotypic stability, and identity of these varieties produced or derived from variety B16#12-9381. Gel electrophoresis is particularly useful in wheat. Wheat variety identification may occur, for example, through electrophoresis of gliadin, glutenin, albumin and globulin, and total protein extracts.

Disclosed are plant breeding methods in which plant populations as well as individual plants are evaluated for general health, agronomics, and stability at one or more stages. These evaluations can include, but are not limited to, one or more of the following characteristics: plant architecture traits such as seedling coleoptile length, coleoptile color (presence of anthocyanin), juvenile plant growth habit, tillering, plant height, straw strength or lodging, flag leaf carriage at boot stage, leaf width and length, glaucosity of stems, leaves and spikes, pubescence of leaves and spikes, spike shape, spike density, spike awnedness, and plant color through-out stages of growth; plant growth characteristics, such as vernalization requirement, date for first stem joint emergence, heading date, flowering date, physiological maturity date and harvest maturity; tolerance to weather conditions, such as cold tolerance, resistance to heaving, tolerance to wet soils and standing water, drought and heat tolerance; and grain characteristics, such as grain yield, test weight, 1000 kernel weight, grain moisture, grain color, grain shape, grain protein, flour milling yield, and baking characteristics.

Wheat variety B16#12-9381 was assayed and/or planted in field trials and evaluated for a variety of traits and/or characteristics as compared to check varieties. The property (s) of appropriate check varieties include but are not limited to varieties with a similar relative maturity, varieties known to be susceptible to one or more particular diseases, insect, pathogen, field condition, weather condition, soil type or condition, and/or crop management practice, varieties known to be tolerant or resistant to one or more particular diseases, insect, pathogen, field condition, weather condition, soil type or condition, and/or crop management practice, varieties comprising one or more particular marker locus, and/or varieties derived from another appropriate variety or having a particular pedigree. Appropriate choice of check varieties for comparison assures an appropriate baseline and valid qualitative or quantitative assessment of any test varieties.

Wheat variety B16#12-9381 may be tested for various traits including, but not limited to grain yield, test weight, heading date, harvest maturity, plant height, straw strength, pre-harvest sprout tolerance, resistance levels to leaf rust, stripe rust, tan spot, *Septoria tritici* blotch, *Stagnospora nodorum* blotch, powdery mildew, bacterial leaf streak, stem rust, barley yellow dwarf virus, Fusarium (scab), wheat yellow mosaic virus and soilborne mosaic virus, and grain characteristics such as flour yield, flour protein, and baking characteristics.

Wheat variety B16#12-9381, being substantially homozygous, may also be reproduced by planting seeds of the line, growing the resulting wheat plants under self-pollinating or sib-pollinating conditions, and harvesting the resulting seed, using techniques familiar to the agricultural arts.

In one aspect, wheat plants, plant parts and seeds are provided which have all or essentially all of the characteristics set forth in Tables 2-6. In one aspect wheat plants, plant parts and seeds are provided which have the physiological and morphological characteristics of wheat variety B16#12-9381, or all of the phenotypic characteristics of wheat variety B16#12-9381, representative seed having been deposited with the ATCC as disclosed herein.

Wheat variety B16#12-9381 may be further reproduced by tissue culture and regeneration. Tissue culture of various tissues of wheat and regeneration of plants therefrom is well known and widely published. Thus, in another aspect provided are cells which upon growth and differentiation produce wheat plants capable of having the physiological and morphological characteristics of wheat variety B16#12-9381.

As used herein, the term "plant parts" includes, without limitation, plant protoplasts, plant cell tissue cultures from which wheat plants can be regenerated, plant calli, plant clumps, plant cells, embryos, pollen, ovules, pericarp, seed, flowers, florets, heads, spikes, stems, stalks, leaves, roots, root tips, anthers, and the like. When indicating that a plant is crossed or selfed this indicates that any plant part of the plant can be used. For instance the plant part does not need to be attached to the plant during the crossing or selfing, only the pollen might be used. Thus, in one embodiment described herein is a plant, plant part, seed, or plant cell of wheat variety B16#12-9381, representative seed of said variety having been deposited under ATCC accession number PTA-127364.

Transgenes and transformation methods provide means to engineer the genome of plants to contain and express heterologous genetic elements, including but not limited to foreign genetic elements, additional copies of endogenous elements, and/or modified versions of native or endogenous genetic elements, in order to alter at least one trait of a plant in a specific manner. Any heterologous DNA sequence(s), whether from a different species or from the same species, which are inserted into the genome using transformation, backcrossing, or other methods known to one of skill in the art are referred to herein collectively as transgenes. The sequences are heterologous based on sequence source, location of integration, operably linked elements, or any combination thereof. Thus, or more transgenes of interest may be introduced into wheat variety B16#12-9381. Transgenes may allow for one a wheat variety B16#12-9381 having one or more desired traits such as herbicide resistance, insect resistance, disease resistance, decreased phytate, modified fatty acid profile, modified fatty acid content, carbohydrate metabolism, protein content, or oil content. Any suitable gene of interest may be engineered into wheat variety B16#12-9381 described herein.

Methods of developing a backcross conversion for wheat variety B16#12-9381 are also provided herein, including the step of repeated backcrossing to wheat variety B16#12-9381. The number of backcrosses made may be 2, 3, 4, 5, 6, 7, 8 or greater, and fewer than 50, 40, 30, 25, 20, 15, 10, 9, or 8. The specific number of backcrosses used will depend upon the genetics of the donor parent and whether molecular markers are utilized in the backcrossing program. Provided are plants and plant populations that are produced from backcrossing methods, transformation, locus conversion, or otherwise produced, and combinations thereof and that retain at least 70%, 75%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, or 99.9% or 99.95%, 99.98%, 99.985%, 99.99% or 99.995% of the genetic profile of wheat variety B16#12-9381. The percentage of the genetics retained in the backcross conversion may be measured by either pedigree analysis or through the use of genetic techniques such as molecular markers or electrophoresis. Such methods and techniques are described in U.S. Pat. No. 8,809,654, the disclosure of which is herein incorporated by reference with regard to this background teaching. The backcross conversion or locus conversion developed from this method may be similar to B16#12-9381 to the results listed in Tables 2-6. Such similarity may be measured by a side by side phenotypic comparison, with differences and similarities determined at a 5% significance level, when appropriate in environmental conditions that account for the trait being transferred.

Also described herein are methods for using wheat variety B16#12-9381 in plant breeding and plants and plant populations produced by such methods. For example, wheat variety B16#12-9381 may be crossed with another variety of wheat to form a first generation population of F1 plants. This first generation population of F1 plants may comprise a complete set of the alleles of wheat variety B16#12-9381. Also provided herein are methods and plants which use transgenic or backcross conversions of wheat variety B16#12-9381 to produce first generation F1 plants.

A method of developing a B16#12-9381-progeny wheat plant comprising crossing wheat variety B16#12-9381 with a second wheat plant and performing a breeding method is also described herein. An exemplary method for producing a line derived from wheat variety B16#12-9381 is as follows. Wheat variety B16#12-9381 may be crossed with another variety of wheat, such as an elite variety. The F1 seed derived from this cross may be grown to form a homogeneous population. The F1 seed contains one set of the alleles from wheat variety B16#12-9381 and one set of the alleles from the other wheat variety. The F1 genome is 50% wheat variety B16#12-9381 and 50% of the other elite variety. The F1 seed is grown and allowed to self, thereby forming F2 seed. On average the F2 seed would have derived 50% of its alleles from wheat variety B16#12-9381 and 50% from the other wheat variety, but various individual plants from the population may have a much greater percentage of their alleles derived from wheat variety B16#12-9381. The F2 seed may be grown and selection of plants made based on visual observation and/or measurement of traits. The wheat variety B16#12-9381-derived progeny that exhibit one or more of the desired wheat variety B16#12-9381-derived traits are selected and each plant may be harvested separately. The F3 seed from each plant may be grown in individual rows and allowed to self. Then selected rows or plants from the rows are harvested and threshed individually. The selections based on visual observation and/or measurements for desirable traits of the plants, such as one or more of the desirable wheat variety B16#12-9381-derived traits are made. The process of growing and selection is repeated any number of times until a homozygous wheat variety B16#12-9381-derived wheat plant is obtained.

The homozygous wheat variety B16#12-9381-derived wheat plant contains desirable traits derived from wheat variety B16#12-9381, some of which may not have been expressed by the other original wheat variety to which wheat variety B16#12-9381 was crossed and some of which may have been expressed by both wheat varieties but now would be at a level equal to or greater than the level expressed in wheat variety B16#12-9381. The homozygous B16#12-9381-derived wheat plants have, on average, 50% of their genes derived from wheat variety B16#12-9381, but various individual plants from the population may have a much greater percentage of their alleles derived from wheat variety B16#12-9381. The breeding process, of crossing, selfing, and selection may be repeated to produce another population of B16#12-9381-derived wheat plants with, on average, 25% of their genes derived from wheat variety B16#12-9381, and with various individual plants from the population having a much greater percentage of their alleles derived from wheat variety B16#12-9381. Homozygous B16#12-9381-derived wheat plants that have received B16#12-9381-derived traits are also provided. Thus, one aspect described herein is a wheat seed produced from (i) selfing the plant or plant part described herein or (ii) crossing of the plant or plant part of described herein, once with a different wheat plant or plant part. Another aspect described herein is a wheat plant or plant part produced by growing the wheat seed described herein. In one aspect, the seed is an F1 hybrid wheat seed.

In some instances, selection may or may not occur at every selfing generation, selection may occur before or after the actual self-pollination process occurs, or individual selections may be made by harvesting individual spikes, plants, rows or plots at any point during the breeding process described herein. In addition, double haploid breeding methods may be used at any step in the process. In one aspect, the population of plants produced at each and any generation of selfing, each such population consisting of plants containing approximately 50% of its genes from wheat variety B16#12-9381, 25% of its genes from wheat variety B16#12-9381 in the second cycle of crossing, selfing, and selection, 12.5% of its genes from wheat variety B16#12-9381 in the third cycle of crossing, selfing, and selection, and so on.

Also disclosed are methods of obtaining a homozygous B16#12-9381-derived wheat plant by crossing wheat variety B16#12-9381 with another variety of wheat and applying double haploid methods to the F1 seed or F1 plant or to any generation of B16#12-9381-derived wheat obtained by the selfing of this cross.

In addition, methods for producing B16#12-9381-derived wheat plants are provided, by crossing wheat variety B16#12-9381 with a wheat plant and growing the progeny seed, and repeating the crossing or selfing along with the growing steps with the B16#12-9381-derived wheat plant from 1 to 2 times, 1 to 3 times, 1 to 4 times, or 1 to 5 times. Thus, any and all methods using wheat variety B16#12-9381 in breeding, including selfing, pedigree breeding, backcrossing, hybrid production and crosses to populations are provided. Unique starch profiles, molecular marker profiles and/or breeding records can be used to identify the progeny lines or populations derived from these breeding methods. Another aspect described herein is a method of producing a progeny seed, the method comprising crossing the wheat plant described herein, to a plant of wheat variety B16#12-9381, representative seed of said variety having been deposited under ATCC accession number PTA-127364 and producing a progeny seed. In another aspect, the method further comprises crossing a plant grown from the progeny seed to a plant of wheat variety of B16#12-9381 and producing a back-crossed seed. In another aspect is the backcrossed seed produced by the methods described herein. In another aspect is a method for producing a second wheat plant, the method comprising applying plant breeding techniques to the wheat plant or plant part described herein, wherein application of said techniques results in the production of a second wheat plant. In another aspect is a method for producing a second wheat plant, the method comprising a doubling haploid seed generated from a cross of the wheat plant or plant part described herein, with a different wheat plant.

Also disclosed are methods of harvesting the grain of variety wheat variety B16#12-9381 and using the grain as seed for planting. Embodiments include cleaning the seed, treating the seed, and/or conditioning the seed. Cleaning the seed includes removing foreign debris such as weed seed and removing chaff, plant matter, from the seed. Conditioning the seed can include controlling the temperature and rate of dry down and storing seed in a controlled temperature environment. Seed treatment is the application of a composition to the seed such as a coating or powder. Seed material can be treated, typically surface treated, with a composition comprising combinations of chemical or biological herbicides, herbicide safeners, pesticides, insecticides, fungicides, nutrients, germination inhibitors, germination promoters, cytokinins, nutrients, plant growth regulators, antimicrobials, and activators, bactericides, nematicides, avicides, or molluscicides.

These compounds are typically formulated together with further carriers, surfactants or application-promoting adjuvants customarily employed in the art of formulation. The coatings may be applied by impregnating propagation material with a liquid formulation or by coating with a combined wet or dry formulation. Examples of the various types of compounds that may be used as seed treatments are provided in The Pesticide Manual: A World Compendium, C. D. S. Tomlin Ed., published by the British Crop Production Council. Some specific seed treatments that may be used on crop seed include, but are not limited to, abscisic acid, acibenzolar-S-methyl, avermectin, amitrol, azaconazole, azospirillum, azoxystrobin, *bacillus, Bacillus subtilis, Bacillus simplex, Bacillus firmus, Bacillus amyloliquefaciens, Pasteuria* genus (e.g. *P. nishizawae*), *Bradyrhizobium*, captan, carboxin, chitosan, clothianidin, copper, cyazypyr, difenoconazole, etidiazole, fipronil, fludioxonil, fluquinconazole, flurazole, fluxofenim, GB126, Harpin protein, imazalil, imidacloprid, ipconazole, isofavenoids, lipo-chitooligosaccharide, mancozeb, manganese, maneb, mefenoxam, metalaxyl, metconazole, PCNB, penflufen, penicillium, penthiopyrad, permethrine, picoxystrobin, prothioconazole, pyraclostrobin, rynaxypyr, S-metolachlor, saponin, sedaxane, TCMTB, tebuconazole, thiabendaxole, thiamethoxam, thiocarb, thiram, tolclofos-methyl, triadimenol, trichoderma, trifloxystrobin, triticonazole and/or zinc.

Seed varieties and seeds with specific genetic resistance traits may be tested to determine which seed treatment options and application rates will complement such varieties and genetic resistance traits in order to enhance yield. For example, a variety with good yield potential but loose smut susceptibility will benefit from the use of a seed treatment that provides protection against loose smut. Likewise, a variety encompassing a genetic resistance trait conferring insect resistance will benefit from the second mode of action conferred by the seed treatment. Further, the good root establishment and early emergence that results from the proper use of a seed treatment will result in more efficient nitrogen use, a better ability to withstand drought and an overall increase in yield potential of a variety or varieties containing a certain trait when combined with a seed treatment.

Thus another aspect described herein is a method comprising cleaning the seed described herein. In another aspect the method further comprises a seed treatment on the surface of the seed.

Wheat variety B16#12-9381 has traits and characteristics that distinguish it from other wheat varieties. A description of the traits used to measure or characterize a wheat variety such as variety B16#12-9381 and the scoring ranges used for such traits are described below in Tables 2-6 and the examples below.

It will be apparent to those of skill in the art that variations may be applied to the compositions and methods described herein and in the steps or in the sequence of steps of the method described herein without departing from the concept, spirit and scope of the invention. More specifically, it will be apparent that certain changes and modifications such as single gene conversions, including for example, modifications and mutations, somoclonal variants, variant individuals selected from large populations of the plants of the instant inbred and the like may be practiced. All such similar substitutes and modifications apparent to those skilled in the art are deemed to be within the spirit, scope and concept of the invention. It is to be understood that the invention is not limited in its application to the details of construction and the arrangement of components described herein.

EXAMPLES

Example 1. Breeding History of Wheat Variety B16#12-9381

B16#12-9381 is a soft red winter wheat, having medium height, medium early maturing awnless wheat variety bred for release by Grow Pro Genetics LLC. B16#12-9381 is an awnless variety selected for grain yield test weight, maturity and disease resistance in its primary area of adaptation; the wheat growing areas of South Carolina, North Carolina, Missouri, Louisiana, Virginia, Pennsylvania, and testing in Illinois. A doubled haploid breeding system was used to create B16#12-9381. Doubled haploidization is a well-known and published process used to create pure lines from segregating populations (Wong et al, 2017; Inagaki, M. N. (2003)). We achieve haploidy by fertilizing emasculated florets with maize pollen (distant hybridization) and then rescuing developed embryos. Chromosomes are then doubled by treatment with colchicine and surviving plants grown out in greenhouses. Once plants reach maturity, the heads are threshed and planted in either single row, 2 row, 4 row, or 12 row plots in a field nursery, depending on how many seeds are harvested from each new doubled haploid plant. Seed from headrows are then planted in single replication observation plots and a small aliquot of seed is kept back for growout. Tissue is sampled from this growout and DNA extracted for marker assisted selection (MAS). Genetic markers have been used for a decade or more in helping to select superior lines based on genotype. Markers for genes that were utilized to identify specific traits include but are not limited to: stripe (yellow) rust resistance, leaf rust resistance, barley yellow dwarf resistance, powdery mildew resistance, soil borne mosaic virus resistance, fusarium head blight resistance, stem rust resistance, photoperiod sensitivity, plant height/dwarfing, vernalization, grain color, and high kernel weight. Once lines are selected from superior marker profiles, superior agronomics, or both, they are placed into multi-year, multi-location yield trials where advancement is contingent upon high grain yield, adequate grain test weight, reliable agronomics, and potential resistance to pathogens.

Once lines advance to multi-location, multi-replication, multi-year testing, 100 heads are selected from the F7 or F(x)DH3 generation and grown out in purification headrows. Each head is planted in a single row, and the best rows are tagged for advancement while off type rows are eliminated before harvest. Tagged rows are harvested individually and then planted out in 40 ft×5 ft long plots the following fall. These plots are rated for trueness to type, rogued for off types, and selected plots are then harvested and bulked together to create breeders seed.

A doubled haploid breeding system was used to create B16#12-9381. A single cross was made in the spring of 2013 in a greenhouse in Bay, AR between B09-2950 and Beretta-5. B09-2950 is an AgriPro release with the parentage of B990081/P961341A3-2-2. Beretta-5 is a short vernalization selection from Beretta, an AgriPro released variety. F1 seed harvested from the cross of B09-2950/Beretta-5 was assigned a cross number of SS13100041. F2 plants were sampled for marker assisted selection and selected plants were then submitted for double haploidisation. A total of 91 doubled haploid lines were produced from these plants and planted in headrows at Bay, AR in 2015, where a headrow plot was selected in the spring of 2016 and assigned the code B16#12-9381.

TABLE 1

Breeding history of wheat variety B16#12-9381

| Year | GENCD | Detail of Stage | Selection criteria |
|------|-------|-----------------|--------------------|
| 2013 | F1 | B09-2950 crossed to BERETTA-5 in greenhouse in Bay, AR | |
| 2014 | F2 | B09-2950/BERETTA-5 was selfed in a greenhouse in Junction City, KS and sampled for marker assisted selection. Selected plants were then submitted to a double haploidisation laboratory. | |
| 2015 | F2HD | 91 DH lines were harvested and planted in headrow plots in Bay, AR. | Height, maturity, disease resistance. |
| 2016 | F2HD1 | Headrow plot was selected and assigned as B16#12-9381. An increase was planted in Bay, AR for plot testing and head purification selection. | All further generations advanced based on |
| 2017 | F2HD2 | Increase was rogued for offtypes and heads selected for purification rows based on trueness to type. 120 purification headrows were planted in Bay, AR. | grain yield, test weight, agronomics, and disease resistance. |
| 2018 | F2HD3 | 22 purification headrows were selected for trueness to type and harvested. These 22 progeny plots were planted in Eaton, CO for increase. | |
| 2019 | F2HD4 | 10 progeny plots are rogued, selected | |

TABLE 1-continued

| Breeding history of wheat variety B16#12-9381 | | | |
|---|---|---|---|
| Year | GENCD | Detail of Stage | Selection criteria |
| | | and harvested based on trueness to type. Breeders seed production is planted in Virginia. | |
| 2020 | F2HD5 | Breeders seed increase is rogued for purity and harvested. Breeders seed sent to foundation. | |

Example 2

Yield and other agronomic responses obtained from test locations that support the area of adaptation. Provide data from at least two years and two locations within the area of adaptation for yield and agronomic response traits. Include and identify at least one recognized check variety for comparing agronomic data.

Disease and insect reactions if any such reactions are stated as varietal attributes. Provide testing conditions used to determine reactions (e.g., field, greenhouse, or laboratory; identity of testing methods). State specific races or strains of organisms, if known. Include and identify susceptible and resistant checks for comparative pest reactions. to *Septoria triticii*.

A line that is selected for advancement from observation plots to yield trials then enters a testing regime that further identifies yield levels, agronomic profile, disease resistance traits, and end use quality over a variety of growing environments. Data collection was performed according to methods known in the art. Collecting data over a wide geographic range provides a robust product profile that enhances the acceptance of a variety once it reaches the release stage. The following table describes the number of potential data points collected on a line as it advances through testing stages.

| Year of Yield Testing | Number of Replications | Number of Locations |
|---|---|---|
| 1 | 10 | 9 |
| 2 | 51 | 26 |
| 3 | 63 | 32 |
| 4 | 63 | 32 |

Year of Yield Testing Number of Replications Number of Locations

TABLE 1a

| Summary of data collection locations for B16#12-9381 in 2020 and 2021. | | | | |
|---|---|---|---|---|
| Location | Sub Region | 2019 | 2020 | 2021 |
| Charleston, MO | Delta | X | X | X |
| Hopkinsville, KY | Delta | X | | |
| Union City, TN | Delta | X | | |
| Trenton, TN | Delta | | X | |
| Dyersburg, TN | Delta | X | | X |
| Harrisburg, AR | Delta | | X | |
| Killen, AL | Delta | | X | |
| Winnsboro, LA | Delta | X | X | X |
| Belvedere, NC | Southeast | X | X | X |
| Raleigh, NC | Southeast | X | X | X |
| Kinston, NC | Southeast | X | | |

TABLE 1a-continued

| Summary of data collection locations for B16#12-9381 in 2020 and 2021. | | | | |
|---|---|---|---|---|
| Location | Sub Region | 2019 | 2020 | 2021 |
| Union County, NC | Southeast | | X | X |
| Lanexa, VA | Mid Atlantic | | X | |
| Warsaw, VA | Mid Atlantic | X | X | X |
| Mount Joy, PA | Mid Atlantic | | X | X |
| Clayton, DE | Mid Atlantic | | | X |

Certain agronomic data is collected along with grain yield at each location that is tested, such as test weight (pounds of grain per bushel, US Standard for winter wheat is 60 lb/bu). Other agronomic data is collected at a smaller, selected number of sites due to increased phenotypic expression (such as plant height, measured in cm at 2-3 points per plot, or lodging on a 1-9 scale) or timing logistics (such as heading date in days Julian and relative maturity on a 1-9 scale) as follows:

GENERAL

1=Excellent
2=Very Good to Excellent
3=Very Good
4=Very Good to Good
5=Good
6=Fair to Good
7=Fair
8=Fair to Poor
9=Poor
10=Not available Disease ratings are captured on an opportunistic basis when evaluating plots for other reasons, such as uniformity and correct layout. However, there are a few observation nurseries that are planted with the objective of collecting specific disease ratings. Examples include but are not limited to, fusarium head blight, leaf rust and soil borne mosaic virus. Not every disease is observed each season and ratings can be subject to change based on changes in disease pressure and race changes, but the scale below indicates a general description of the ratings made.

B16#12-9381 is 10 cm shorter and obtains inflorescence 2 days later than SY Viper. B16#12-9381 is known to have a gene for Barley Yellow Dwarf resistance as indicated by the presence of the marker for BVD2/3. It has moderate levels of native resistance to races of stripe rust, leaf rust and powdery mildew, along with moderate susceptibility to Fusarium head blight. B16#12-9381 also indicates resistance to Hessian fly races B, C, and D. For milling and baking quality, B16#12-9381 exhibits test weight equal to that of SY Viper, good cookie baking, and acceptable milling properties. The results are described Tables 2-6.

TABLE 2

| Wheat Variety B16#12-9381 Description Information | |
|---|---|
| Wheat Description | |
| Kind of wheat | Common, soft red |
| Seasonal Growth Habit | Winter |
| Coleoptile Color | White- |
| Juvenile Growth Habit | Semi-erect |
| Leaf Color at Boot | Green |

TABLE 2-continued

| Wheat Variety B16#12-9381 Description Information | |
| --- | --- |
| Flag Leaf at Boot | Erect, twisted, waxed |
| Auricle Color | White |
| Heading Date/Anthesis: Average number of day(s) to 50% heading | 113 days; 1 day later than SY Viper |
| Anther Color | Yellow |
| Anthocyanin | Absent |
| Plant Height | 83.3 cm; 9 cm shorter than SY Viper |
| Internodes | Hollow |
| Spike Characteristics | |
| Shape | Tapering |
| Density | Mid-dense |
| Curvature | Erect |
| Awns | Awnless |
| Awn Color | N/A |
| Glume Characteristics | |
| Color | White/Amber |
| Length | Medium |
| Shoulder shape | Oblique |
| Shoulder width | Medium |
| Beak Shape | Acute |
| Beak Length | Medium |
| Pubescence | Absent (glabrous) |
| Seed Characteristics | |
| Color | Red |
| Shape | Ovate |
| Cheek | Rounded |
| Brush | Medium |
| Average 1000-Kernal Weight | 32 g, which is 5 grams lighter than SY Viper |

TABLE 3

Summary of yield trial data for B16#12-9381 and selected commercial checks for 2020 and 2021.

| Variety | 2 year overall | 2 Year Delta | 2 Year Southeast (bu/A) | 2 year Mid Atlantic |
| --- | --- | --- | --- | --- |
| | Yield (bu/A) | | | |
| SY 100 | 96.8 | 85.0 | 96.2 | 113.3 |
| GP 747 | 96.6 | 88.6 | 92.4 | 111.5 |
| B16#12-9381 | 92.9 | 80.5 | 97.2 | 105.1 |
| P26R59 | 91.9 | 84.5 | 86.5 | 107.1 |
| P26R36 | 91.8 | 86.5 | 85.4 | 105.3 |
| SY Richie | 89.8 | 77.8 | 96.6 | 98.9 |
| HILLIARD | 89.4 | 86.0 | 81.1 | 102.1 |
| SY Viper | 89.1 | 79.4 | 86.9 | 104.3 |
| Mean | 89.9 | 81.4 | 87.5 | 103.5 |
| Mean of checks | 89.4 | 81.5 | 86.0 | 103.3 |
| # of Locations | 20 | 8 | 6 | 6 |
| # of Reps | 40 | 16 | 12 | 12 |
| LSD (0.05) | 3.6 | 4.9 | 8.0 | 5.7 |
| CV (%) | 6.7 | 5.7 | 9.2 | 4.8 | s. Summary of yield trial data for B16#12-9381 and selected commercial checks for 2019-2021.

| Variety | 3 year overall | 3 Year Delta | 3 Year Southeast (bu/A) | 3 year Mid Atlantic |
| --- | --- | --- | --- | --- |
| | Yield (bu/A) | | | |
| GP 747 | 88.9 | 83.9 | 82.4 | 106.7 |
| P26R36 | 87.2 | 83.6 | 80.8 | 102.3 |
| B16#12-9381 | 87.0 | 78.5 | 88.1 | 101.1 |
| P26R59 | 86.9 | 81.5 | 81.0 | 104.3 |
| HILLIARD | 84.4 | 81.2 | 77.8 | 98.8 |
| SY Richie | 84.3 | 75.4 | 87.9 | 96.2 |
| SY Viper | 83.2 | 78.0 | 76.2 | 101.9 |
| SY 547 | 81.0 | 77.5 | 75.7 | 94.5 |

TABLE 3-continued

| | | | | |
| --- | --- | --- | --- | --- |
| Mean | 84.4 | 79.5 | 78.8 | 101.9 |
| Mean of checks | 84.6 | 80.4 | 78.3 | 101.8 |
| # of Locations | 29 | 13 | 9 | 7 |
| # of Reps | 57 | 26 | 18 | 13 |
| LSD (0.05) | 3.2 | 4.1 | 7.3 | 4.9 |
| CV (%) | 7.2 | 7.4 | 9.5 | 4.0 |

TABLE 4

Summary of agronomic trait data for B16#12-9381 and selected commercial checks collected in 2020 and 2021.

| Variety | Harvest Moisture (%) | Test Weight (lb/bu) | Heading Date (b Julian) | Plant Height (in) | Winter Hardiness (1-9 rating) | Lodging |
| --- | --- | --- | --- | --- | --- | --- |
| B16#12-9381 | 13.9 | 58.1 | 105 | 31.9 | 3 | 1 |
| SY 100 | 14.1 | 56.5 | 107 | 33.4 | 4 | 2 |
| GP 747 | 13.9 | 56.7 | 107 | 34.9 | 5 | 2 |
| P26R59 | 14.3 | 57.8 | 107 | 30.6 | 6 | 2 |
| P26R36 | 13.8 | 58.7 | 107 | 35.3 | 5 | 2 |
| SY Richie | 14.2 | 57.9 | 102 | 33.8 | 3 | 2 |
| HILLIARD | 13.8 | 58.8 | 105 | 35.6 | 6 | 2 |
| SY Viper | 14.8 | 58.9 | 103 | 36.5 | 5 | 2 |
| Mean | 14.1 | 58.1 | 106 | 34.0 | 4 | 2 |
| Mean of checks | 14.1 | 58.2 | 106 | 34.3 | 5 | 2 |
| # of locations | 20 | 20 | 7 | 10 | 1 | 4 |
| # of Reps | 40 | 39 | 14 | 20 | | 8 |
| LSD (0.05) | 0.5 | 0.6 | 1.0 | 0.9 | | 1 |
| CV (%) | 6.6 | 1.3 | 0.6 | 3.1 | | |

TABLE 5a

Disease resistance ratings for B16#12-9381 and selected commercial checks collected in 2020 and 2021.

| Variety | Barley Yellow Dwarf | Hessian Fly | Rust Leaf Rust | Stripe Rust | Powdery Mildew |
| --- | --- | --- | --- | --- | --- |
| | 1-9 Rating: 1 being more resistant, 9 being most susceptible | | | | |
| B16#12-9381 | 3 | 5 | 3 | 5 | 1 |
| SY 100 | 3 | 6 | 7 | 2 | 6 |
| GP 747 | 4 | 6 | 7 | 1 | 3 |
| P26R59 | 7 | 7 | 6 | 2 | 5 |
| P26R36 | 6 | 7 | 4 | 1 | 8 |
| SY Richie | 6 | 6 | 2 | 1 | 3 |
| HILLIARD | 6 | 4 | 5 | 1 | 2 |
| SY Viper | 4 | 5 | 6 | 2 | 5 |
| Mean | 5 | 6 | 4 | 3 | 4 |
| Mean of Checks | 5 | 6 | 5 | 2 | 5 |
| # of Locations | 1 | 1 | 3 | 1 | 1 |
| Year Observed | 2021 | 2020 | 2020-2021 | 2021 | 2021 |
| # of Reps | | | 6 | | |
| LSD (0.05) | | | 1 | | |
| CV(%) | | | 14.2 | | |

TABLE 5b

Disease resistance ratings for B16#12-9381 and selected commercial checks collected in 2020 and 2021.

| Variety | Soil Borne Mosaic | Septoria Glume Blotch | Septoria Leaf Blotch | Fusarium Head Blight |
| --- | --- | --- | --- | --- |
| B16#12-9381 | 3 | 3 | 4 | 5 |
| SY 100 | 5 | 4 | 6 | 6 |
| GP 747 | 3 | 4 | 5 | 6 |
| P26R59 | 4 | 3 | 4 | 7 |

TABLE 5b-continued

Disease resistance ratings for B16#12-9381 and
selected commercial checks collected in 2020 and 2021.

| Variety | Soil Borne Mosaic | Septoria Glume Blotch | Septoria Leaf Blotch | Fusarium Head Blight |
|---|---|---|---|---|
| P26R36 | 2 | 3 | 4 | 3 |
| SY Richie | 5 | 3 | 5 | 9 |
| HILLIARD | 3 | 2 | 3 | 6 |
| SY Viper | 5 | 4 | 5 | 7 |
| Mean | 3 | 3 | 4 | 5 |
| Mean of Checks | 3 | 3 | 4 | 5 |
| # of Locations | 1 | 1 | 2 | 4 |
| Year Observed | 2020 | 2020 | 2020-2021 | 2020-2021 |
| # of Reps | | | 4 | 7 |
| LSD (0.05) | | | 2 | 1 |
| CV (%) | | | 12.4 | 6.4 |

TABLE 6

Milling and baking quality characteristics of B16#12-9381
and known commercial check SY Viper. Results are taken
from one location each in 2018 and 2020.

| Variety | Kernal Protein (%) | Flour Protein (%) | Whole Grain Hardiness (%) | Flour Hardiness (%) | Flour Yield (%) |
|---|---|---|---|---|---|
| B16#12-9381 | 10.1 | 8.8 | 19.5 | 53.0 | 71.4 |
| SY Viper | 10.0 | 8.5 | 11.0 | 34.5 | 68.2 |

| Variety | Break Flour (%) | Cookie Diameter (cm) | Sodium Carbonate (%) | Lactic Acid SRC (%) | Sucrose SRC (%) |
|---|---|---|---|---|---|
| B16#12-9381 | 54.3 | 19.7 | 62.3 | 92.6 | 86.9 |
| SY Viper | 51.3 | 19.5 | 70.7 | 96.5 | 106.1 |

| Variety | Bran (%) | Shorts (%) | Reduction Flour (%) | Water SRC (%) | Top Grain (rating) |
|---|---|---|---|---|---|
| B16#12-9381 | 23.3 | 5.3 | 17.1 | 50.4 | 1.0 |
| SY Viper | 26.0 | 5.8 | 16.9 | 53.0 | 3.0 |

| Variety | Ash (%) |
|---|---|
| B16#12-9381 | 77.9 |
| SY Viper | 77.7 |

Applicant has deposited 2500 seeds of wheat variety B16#12-9381 with the American Type Culture Collection (ATCC), 10801 University Boulevard, Manassas, VA 20110, USA, as ATCC Deposit No. PTA-127364. The seeds deposited with the ATCC on Oct. 7, 2022, are from seed stock maintained by Grow Pro Genetics, LLC, 375 N. Old US Route 66, PO Box #449, Hamel, IL 62046 since prior to the filing date of this disclosure. Access to this seed will be available during the pendency of this application to the Commissioner of Patents and Trademarks and persons determined by the Commissioner to be entitled thereto upon request. Upon allowance of any claims in the application, Applicant will make the deposit available to the public pursuant to 37 C.F.R. § 1.808. This deposit of the Wheat Variety B16#12-9381 will be maintained in the ATCC depository, which is a public depository, for a period of 30 years, or 5 years after the most recent request, or for the enforceable life of the patent, whichever is longer, and will be replaced if it becomes nonviable during that period. Additionally, Applicant has or will satisfy all of the requirements of 37 C.F.R § 1.801-1.809, including providing an indication of the viability, of the sample upon deposit. Applicant has no authority to waive any restrictions imposed by law on the transfer of biological material or its transportation in commerce. Applicant does not waive any infringement of rights granted under this patent or under the Plant Variety Protection Act (7 USC § 2321 et seq.). Unauthorized seed multiplication is prohibited.

What is claimed:

1. A plant, plant part, seed, or plant cell of wheat variety B16#12-9381, representative seed of said variety having been deposited under ATCC accession number PTA-127364.

2. A wheat seed produced from (i) selfing the plant or plant part of claim 1 or (ii) crossing of the plant or plant part of claim 1 once with a different wheat plant or plant part.

3. A wheat plant or plant part produced by growing the wheat seed of claim 2.

4. The wheat seed of claim 2, wherein the seed is an F1 hybrid wheat seed.

5. A method of producing a progeny seed, the method comprising crossing the wheat plant of claim 3, to a plant of wheat variety B16#12-9381, representative seed of said variety having been deposited under ATCC accession number PTA-127364 and producing a progeny seed.

6. The method of claim 5, wherein the method further comprises crossing a plant grown from the progeny seed to a plant of wheat variety of B16#12-9381 and producing a back-crossed seed.

7. A method for producing a second wheat plant, the method comprising applying plant breeding techniques to the wheat plant or plant part of claim 3, wherein application of said techniques results in the production of a second wheat plant.

8. A method for producing a second wheat plant, the method comprising crossing the wheat plant or plant part of claim 3, with a different wheat plant using a doubled haploid breeding system.

9. A method comprising cleaning the seed of claim 1.

10. The seed of claim 1, further comprising a seed treatment on the surface of the seed.

* * * * *